(12) United States Patent
Wallenstein et al.

(10) Patent No.: US 11,324,604 B2
(45) Date of Patent: May 10, 2022

(54) INTERBODY WITH EXTENDIBLE MEMBERS

(71) Applicant: K2M, Inc., Leesburg, VA (US)

(72) Inventors: Todd M. Wallenstein, Ashburn, VA (US); Clint Boyd, Leesburg, VA (US); Jennifer Anne Moore, Leesburg, VA (US); Jordan Floyd, Westlake, OH (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 16/968,393

(22) PCT Filed: Mar. 1, 2019

(86) PCT No.: PCT/US2019/020237
§ 371 (c)(1),
(2) Date: Aug. 7, 2020

(87) PCT Pub. No.: WO2019/173130
PCT Pub. Date: Sep. 12, 2019

(65) Prior Publication Data
US 2020/0390564 A1    Dec. 17, 2020

Related U.S. Application Data

(60) Provisional application No. 62/638,089, filed on Mar. 1, 2019.

(51) Int. Cl.
*A61F 2/44* (2006.01)
*A61F 2/30* (2006.01)

(52) U.S. Cl.
CPC .... *A61F 2/442* (2013.01); *A61F 2002/30565* (2013.01)

(58) Field of Classification Search
CPC ... A61F 2/442; A61F 2/4425; A61F 2002/443
See application file for complete search history.

(56) References Cited

U.S. PATENT DOCUMENTS

| 4,309,777 | A | * | 1/1982 | Patil | A61F 2/442 623/17.13 |
|---|---|---|---|---|---|
| 5,123,926 | A | * | 6/1992 | Pisharodi | A61F 2/441 606/247 |
| 5,702,391 | A | * | 12/1997 | Lin | A61F 2/446 623/17.11 |
| 6,102,950 | A | * | 8/2000 | Vaccaro | A61F 2/447 623/17.16 |
| 6,231,609 | B1 | * | 5/2001 | Mehdizadeh | A61F 2/441 623/17.11 |
| 6,527,803 | B1 | * | 3/2003 | Crozet | A61F 2/442 623/17.11 |
| 6,572,653 | B1 | * | 6/2003 | Simonson | A61F 2/442 606/247 |

(Continued)

OTHER PUBLICATIONS

International Search Report and Written Opinion from PCT/US19/20237, dated May 23, 2019.

*Primary Examiner* — Matthew J Lawson
(74) *Attorney, Agent, or Firm* — Lerner, David, Littenberg, Krumholz & Mentlik, LLP (57) ABSTRACT

An interbody at least one surface including a plurality of members that are independently configured and dimensioned to move from a first position to a second position is disclosed.

9 Claims, 6 Drawing Sheets

(56) References Cited

U.S. PATENT DOCUMENTS

| | | | |
|---|---|---|---|
| 7,270,680 B2 | 9/2007 | Ralph et al. | |
| 7,563,286 B2 | 7/2009 | Gerber et al. | |
| 7,780,733 B2 | 8/2010 | Carver et al. | |
| 8,303,660 B1 * | 11/2012 | Abdou | A61F 2/4611 623/17.14 |
| 8,512,409 B1 * | 8/2013 | Mertens | A61F 2/447 623/17.16 |
| 8,523,946 B1 * | 9/2013 | Swann | A61F 2/4455 623/17.16 |
| 9,707,100 B2 * | 7/2017 | Duffield | A61F 2/4611 |
| 2005/0049590 A1 | 3/2005 | Alleyne et al. | |
| 2005/0251260 A1 * | 11/2005 | Gerber | A61F 2/4425 623/17.13 |
| 2006/0069436 A1 * | 3/2006 | Sutton | A61F 2/4684 623/17.13 |
| 2008/0004704 A1 | 1/2008 | Katz | |
| 2008/0177389 A1 | 7/2008 | Parrish | |
| 2012/0016480 A1 | 1/2012 | Gerber et al. | |
| 2012/0271423 A1 | 10/2012 | Wallenstein et al. | |
| 2013/0013074 A1 * | 1/2013 | Shikinami | A61F 2/442 623/17.16 |

\* cited by examiner

INTERBODY WITH EXTENDIBLE MEMBERS

CROSS-REFERENCE TO RELATED APPLICATIONS

This application is a national phase entry under 35 U.S.C. § 371 of International Application No. PCT/US2019/020237, filed Mar. 1, 2019, which claims the benefit of the filing date of U.S. Provisional Patent Application No. 62/638,089 filed Mar. 3, 2018, the disclosure of which is hereby incorporated herein by reference.

BACKGROUND OF THE INVENTION

The invention relates generally to an interbody at least one surface including a plurality of members that are independently configured and dimensioned to move from a first position to a second position is disclosed.

After a partial or complete discectomy in which a damaged intervertebral disc is removed, a normally occupied space between adjacent vertebral bodies is subject to collapse and/or misalignment due to the absence of all or a part of the intervertebral disc. In such situations, a physician may insert one or more prosthetic interbodies between the affected vertebrae to maintain normal disc spacing and/or the normal amount of lordosis in the affected region. The normally occupied disc space is not a consistent size between vertebrae. Additionally, the disc space is different in different patients. For this reason, prosthetic interbodies are made of varying size and dimensions so that a physician can select an interbody that most closely matches the disc space.

However, current prosthetic interbodies include rigid surfaces that do not mimic the curvatures of the adjacent vertebral bodies. For this reason, gaps are present between the vertebral body and the prosthetic interbody that may take an extended period of time before bone growth has occurred. There exists a possibility that prosthetic interbodies may be dislodged or moved from their desired implantation location due to movement by the patient before sufficient bone growth has occurred.

Therefore, a need exists for prosthetic interbody that provides a desired amount of lordosis, allows for bone growth between adjacent vertebrae, maintains the space between adjacent vertebrae during bone ingrowth, and resists dislocation from its implantation site.

BRIEF SUMMARY OF THE INVENTION

In an aspect, there is disclosed an interbody at least one surface including a plurality of members that are independently configured and dimensioned to move from a first position to a second position.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

Various embodiments of the present disclosure are described herein below with reference to the drawings, wherein.

DETAILED DESCRIPTION

Various embodiments will now be described in detail with reference to the drawings, wherein like reference numerals identify similar or identical elements. Additionally, in the drawings and in the description that follows, terms such as front, rear, upper, lower, top, bottom, and the similar directional terms are used simply for convenience of description and are not intended to limit the disclosure attached hereto.

In the drawings and in the description that follows, the term "proximal" refers to the portion of the device that is closest to the operator, while the term "distal" refers to the portion of the device that is furthest from the operator. Additionally, in the drawings and in the description that follows, terms such as front, rear, upper, lower, top, bottom, and the similar directional terms are used simply for convenience of description and are not intended to limit the disclosure attached hereto. In addition, the term "cephalad" is used to indicate a direction toward a patients head, whereas the term "caudad" indicates a direction toward the patient's feet. Further still, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

Figure 1A:
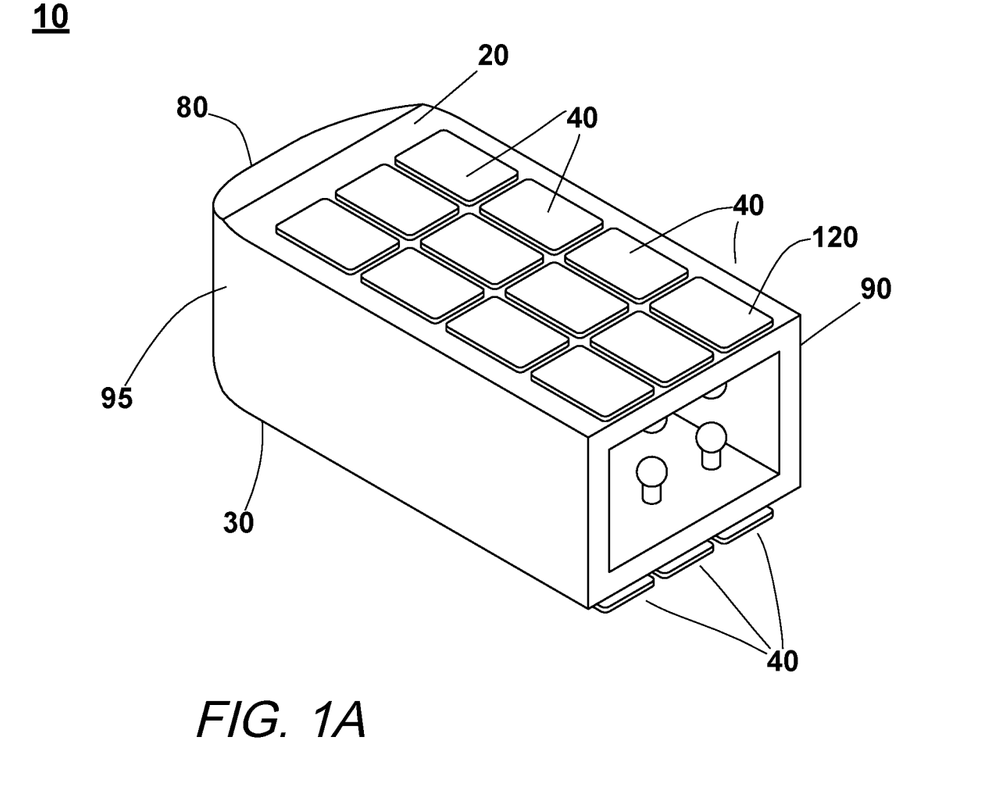
FIG. 1A is an isometric view of an interbody with a plurality of members in a first position.
Figures 1B, 1C:
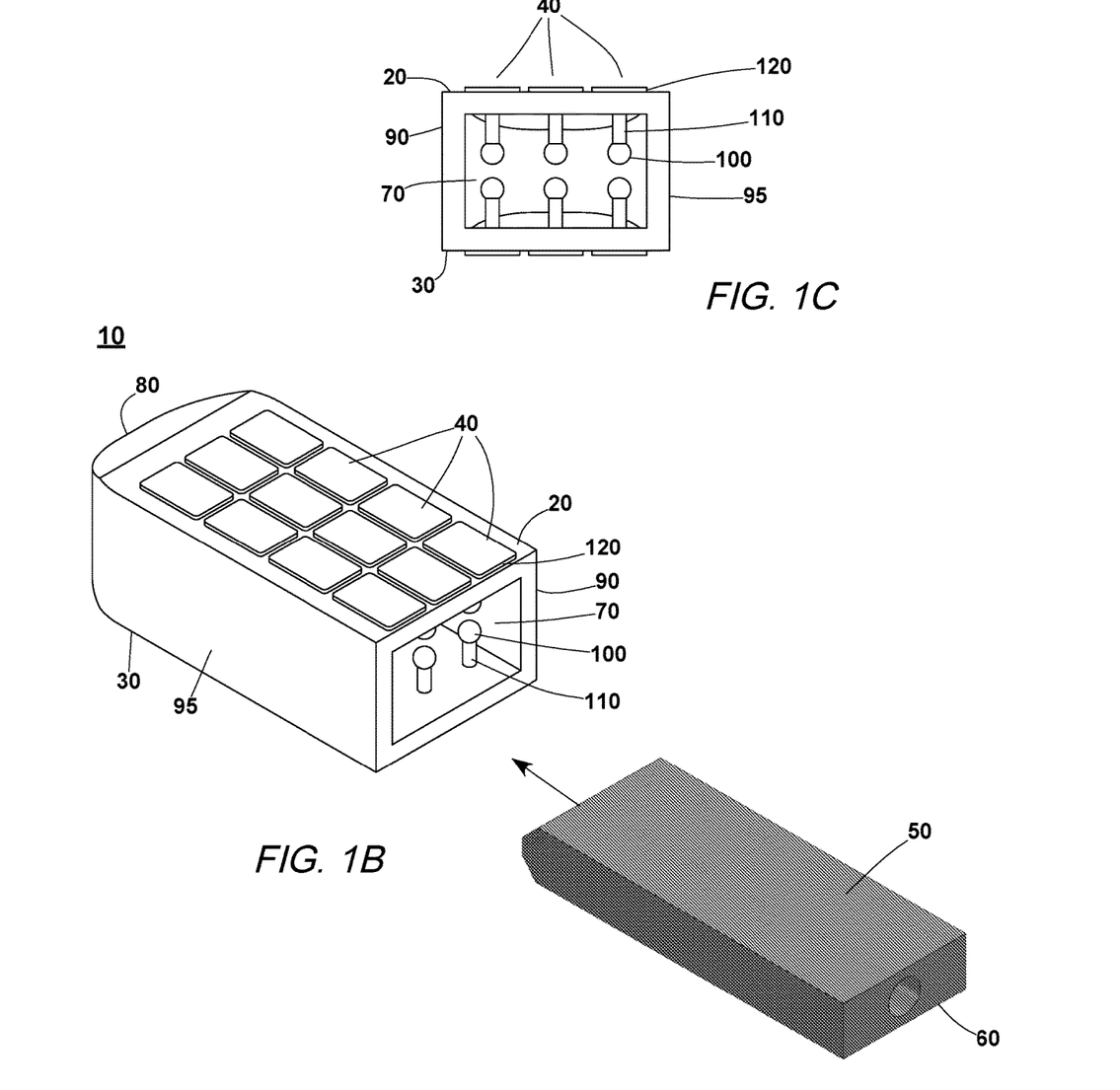
FIG. 1B is an exploded view of an interbody with a plurality of members in a first position and a block.
FIG. 1C is an end view of FIG. 1A.

FIGS. 1A-1C illustrate an interbody 10 including at least one surface including a plurality of members 40 that are independently configured and dimensioned to move from a first position to a second position. Each member of the plurality of members can move independent of each other or in conjunction with one or more members. The interbody 10 can include up to 6 surfaces, such as a top surface 20, a bottom surface 30, a front surface 80, a first side surface 90, a second side surface 95, and a back surface. As shown in FIG. 1A, an interbody 10 can include at least one surface, such as the top surface 20, including a plurality of members 40. As shown in FIG. 1B, an interbody 10 can include at least one surface, such as the top surface 20 and the bottom surface 30, including a plurality of members 40. It will be appreciated that although a top surface 20 and a bottom surface 30 include the plurality of members 40 and face adjacent vertebral bodies, as shown in the Figures, alternative configurations are possible. For example, the interbody 10 can be placed so that the top surface 20 and the bottom surface 30 with their plurality of members are placed to fulfill a width of the disc space. As a further example, a first side surface 90 and a second side surface 95 can include the plurality of members 40 and can be used fulfill a dimension of the disc space.

Figure 2A:
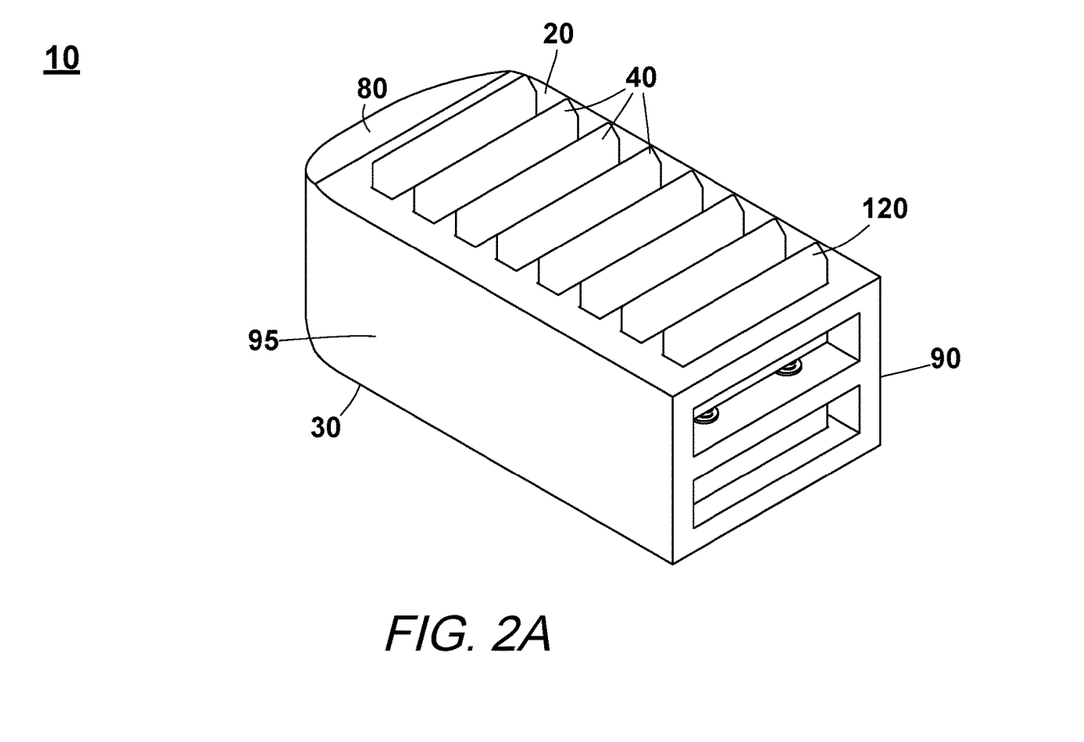
FIG. 2A is an isometric view of an interbody according to another aspect of the invention.
Figure 2B:
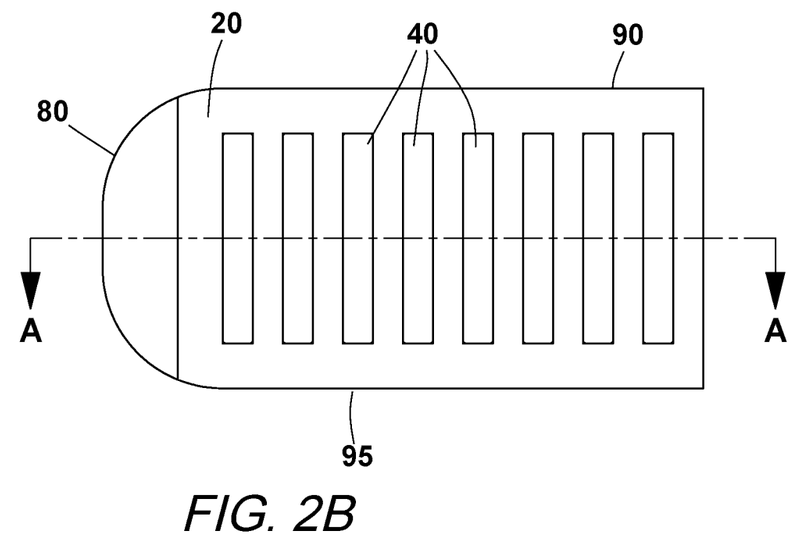
FIG. 2B is a top view of FIG. 2A.

As shown in FIGS. 1A, 1B, 2A, and 2B, the plurality of members 40 can be present in an array on the at least one surface. The plurality of members 40 can be present on the entire surface. In another aspect, the plurality of members can be present on a portion of the surface. As shown in FIG. 2B, the plurality of members 40 can be present in an array of bars on the at least one surface that extend from a first side surface 90 to a second side surface 95. It is contemplated that the plurality of members 40 can be present in an array of bars on the at least one surface that extend from a front surface 80 to a back surface.

Figure 2C:
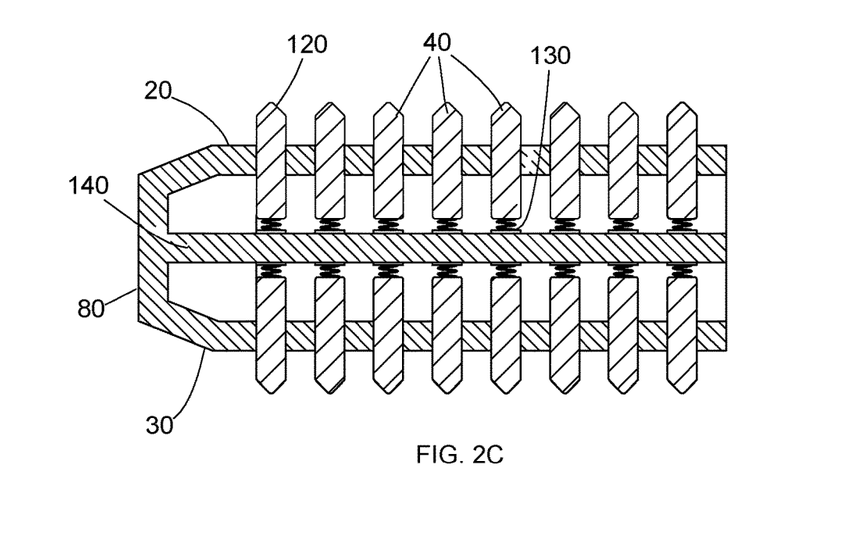
FIG. 2C is a cross-section of FIG. 2B along line A-A.

As shown in FIG. 1C, each member of the plurality of members 40 can include a first end 120, a shaft 110, and a second end 100. The first end 120 of the member 40 can be configured and dimensioned to any size and shape. As shown in FIGS. 1A-1C, the first end 120 is a flat, smooth-surface, rectangular shape. In an aspect, the first end 120 can be curved, such as concave or convex. In another aspect, as shown in FIGS. 2A-2C, the first end 120 can be pointed, such as in the form of teeth having two angled surfaces. The first end 120 can also include a roughened surface, such as by etching, to promote osteogenesis. Additionally, the first end 120 can include a plurality of teeth to create a surface that can engage with adjacent vertebral bodies to inhibit movement of the interbody 10 between vertebral bodies.

The shaft 110 of each member of the plurality of members 40 can be configured and dimensioned to provide support to the member 40. The shaft 110 can be formed from a material that provides rigidity to the member, such as metal. The shaft 100 can have a thickness that provides rigidity to the member 40. In an aspect, the shaft 110 provides rigidity to the member 40 to limit or hinder bending during insertion of the interbody 10 into a space between vertebral bodies.

In another aspect, the shaft 110 can be formed from a material that provides flexibility or deformability to the member, such as a polymer. The shaft 110 can have a thickness that provides flexibility or deformability to the member 40. In another aspect, the shaft 110 can include a flexible pattern that provides flexibility to the member 40. The shaft 110 can bend during insertion of the interbody 10 into a space between vertebral bodies.

Figure 2D:
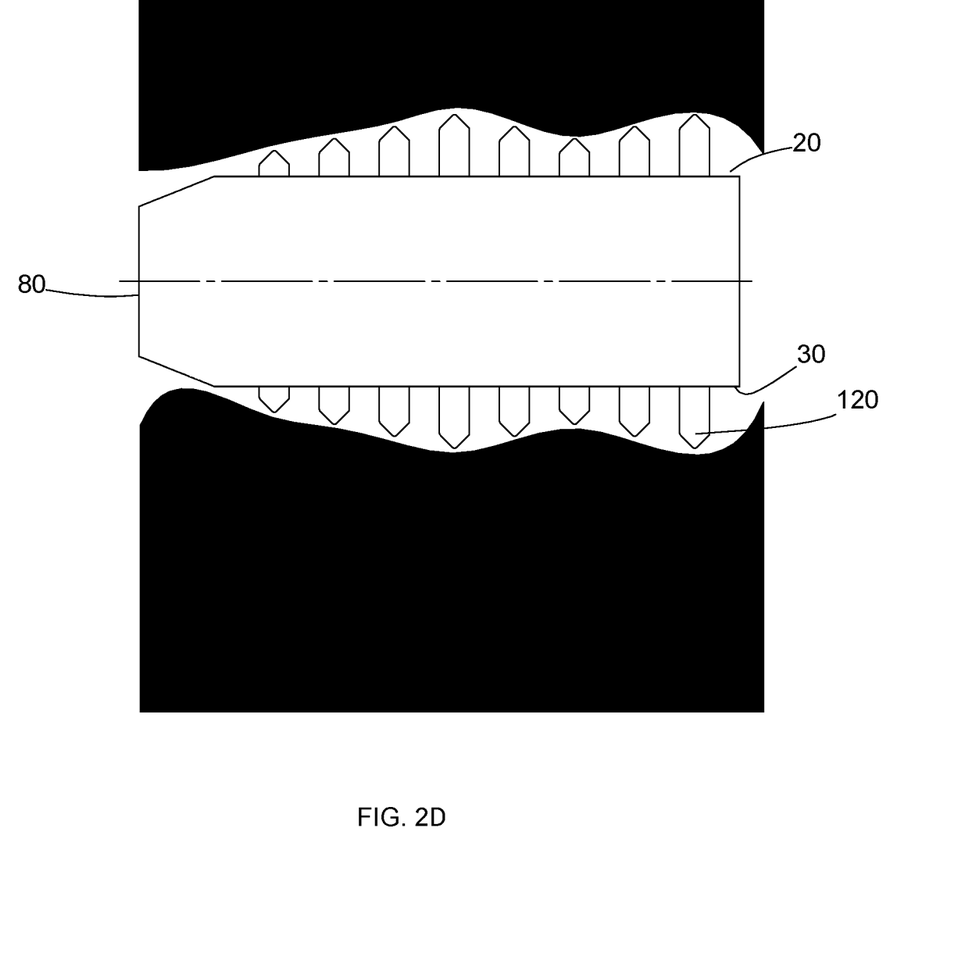
FIG. 2D illustrates the interbody of FIG. 2A in a space between vertebral bodies.

The member 40 can also include a spring 130. The spring 130 can be any form that provides flexibility, such as a helical spring, a wave spring, or belleville washers. As shown in FIG. 2C, the spring 130 can be present at a second end 100 of the member 40. The spring 130 can attach the second end 100 of the member 40 to a beam 140 that extends a length of the interbody 10. In this manner, each member 40 of the plurality of members can be independently extended or decompressed, as shown in FIG. 2D, as the interbody 10 is inserted into a space between vertebral bodies. The increased contact between the plurality of member 40 of the interbody 10 can reduce the likelihood of expulsion of the interbody 10.

Figure 3A:
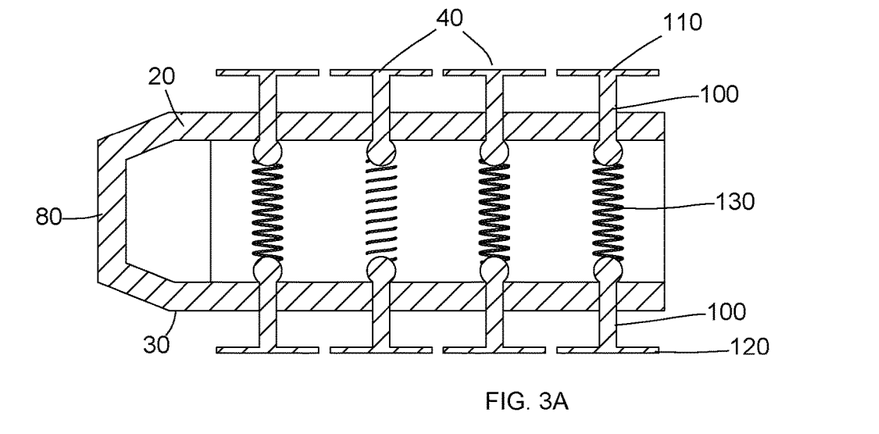
FIG. 3A is a cross-section of an interbody according to another aspect of the invention.
Figure 3B:
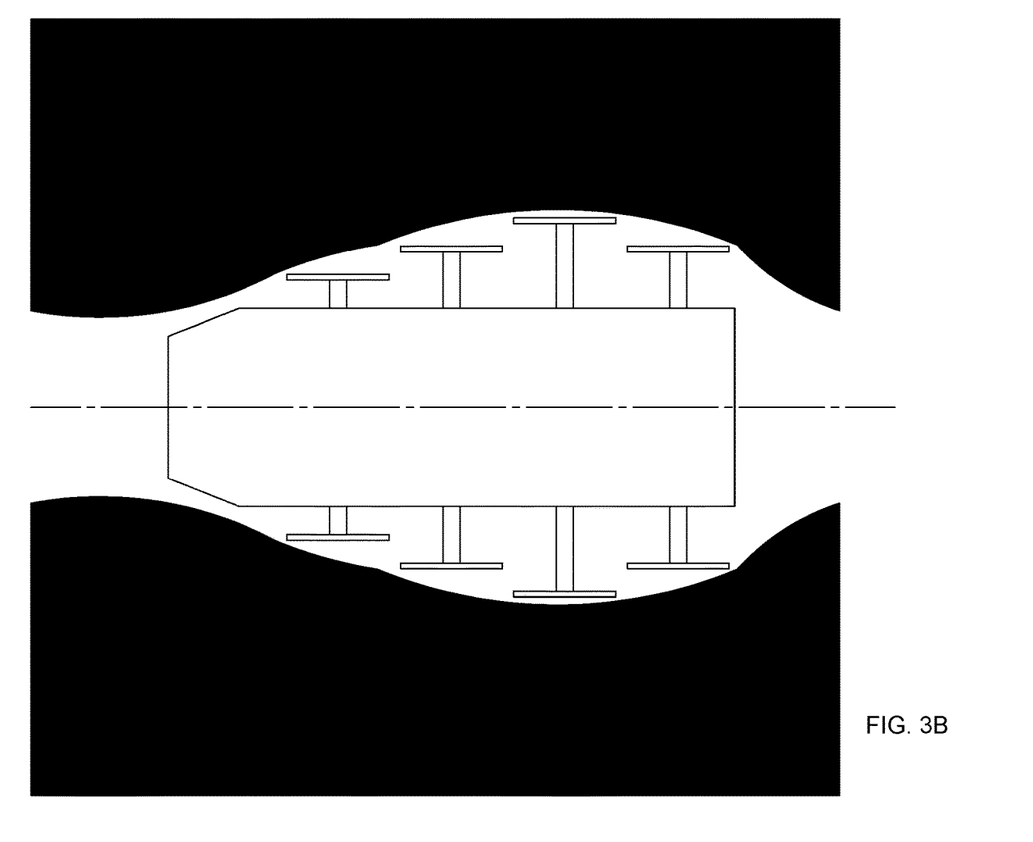
FIG. 3B illustrates the interbody of FIG. 3A in a space between vertebral bodies.

In another aspect, the member 40 can include a first end 120, a shaft 110, a spring 130, and a second end 100, as shown in FIG. 3A. A force applied to the first end 120 of a member 40 on a top surface 20 could push the member 40 to extend further below the bottom surface 30 of the interbody. In another aspect, a force applied to both a first end 120 and a second end 100 of a member 40 could decompress the spring 130 with an interior of the interbody 10. In this manner, each member 40 could independently be extended or decompressed when the interbody 10 is inserted into a space between vertebral bodies, as shown in FIG. 3B.

Referring back to FIG. 1C, the member 40 can include a second end 100. The second end 100 can be configured and dimensioned to prevent the member 40 from separating from the interbody 10. As shown in FIG. 1C, the second end 100 can be spherically shaped although any shape can be used so long as it is larger than an opening in the interbody 10. In an aspect, the member 40 does not include a second end 100. In another aspect, the second end 100 can be attached to a spring 130.

The interbody 10 can include an array of openings (not shown) on the at least one surface that includes the plurality of member 40. For example, the interbody 10 of FIGS. 1A-1C would include a plurality of circular openings that are configured and dimensioned to receive the shaft 110 of the plurality of member 40. As another example, the interbody 10 of FIGS. 2A-D would include a plurality of slot openings that are configured and dimensioned to receive the shaft 110 (in the form of elongated bars) of the plurality of member 40.

Referring back to FIGS. 1A-1C, the plurality of members 40 can be present in a first position, i.e., the first end 120 of the plurality of members 40 abuts against the at least one surface and the second end 100 of the plurality of members 40 extends into the interior space 70 of the interbody 10. In order to extend the plurality of members 40 a block 50 is inserted into the interior space 70. A front end of the block 50 can be configured and dimensioned to facilitate insertion of the block 50 into the interior space 70 and between the oppositely oriented second ends 100 of the plurality of members 40 that can be present on the top surface 20 and the bottom surface 30. The block 50 can include a hole 60 configured and dimensioned to receive an insertion tool (not shown). With the inclusion of the block 50 into the interbody 10, all of the plurality of members 40 extend into the second position without any varying extension.

Alternatively, the plurality of members 40 of the interbody 10 illustrated in FIGS. 2A-2C and 3A are fully extended into the second position when the interbody 10 is not present between vertebral bodies. Upon insertion, as show in FIGS. 2D and 3B, the plurality of members 40 can each independently compress to the first position, or any position therebetween, into the interior space 70 due to the presence of the spring 130 on the plurality of members 40.

The interbody 10 can be formed of any material that is bio-compatible. The interbody 10 can be formed by known manufacturing methods, such as additive manufacturing, e.g., three-dimensional printing; chemical etching; photo etching; laser cutting; water jet cutting; and traditional machining, etc.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. An interbody implant comprising:
   a top surface, a bottom surface, a first side surface, a second side surface, and a front surface defining an interior space of a first body; and at least one surface including a two-dimensional array of a plurality of members comprising a shaft extending along an axis between a first end and a second end of the respective member, each shaft extending through an opening in the at least one surface such that the first end is positioned outside of the first body and the second end is positioned in the interior space of the first body, the first end being wider than a portion of the shaft extending through the opening, wherein each of the plurality of members is configured and dimensioned to move independently from a first position to a second position by axial translation of the respective shaft through the opening.

2. The interbody implant of claim 1, wherein the top surface includes a plurality of the openings.

3. The interbody implant of claim 1, wherein the bottom surface includes a plurality of the openings.

4. The interbody implant of claim 1, further comprising a spring.

5. The interbody implant of claim 1, wherein each of the second ends of the plurality of members is spherically shaped and has a larger dimension transverse to the axis of the respective shaft than the opening through which the shaft extends.

6. The interbody implant of claim 1, wherein a second body is configured and dimensioned to facilitate insertion into and translation within the interior space of the first body.

7. The interbody implant of claim 1, wherein each of the shafts has a uniform thickness along the axis of the respective shaft.

8. The interbody implant of claim 1, wherein the first end is a curved surface.

9. The interbody implant of claim 1, wherein the first end is a rough surface.

* * * * *

UNITED STATES PATENT AND TRADEMARK OFFICE
CERTIFICATE OF CORRECTION

PATENT NO. : 11,324,604 B2  
APPLICATION NO. : 16/968393  
DATED : May 10, 2022  
INVENTOR(S) : Todd M. Wallenstein et al.

It is certified that error appears in the above-identified patent and that said Letters Patent is hereby corrected as shown below:

On the Title Page

Item (60), Related U.S. Application Data, after Provisional application No. 62/638,089, delete "filed on Mar. 1, 2019" and insert --filed on Mar. 3, 2018--.

Signed and Sealed this
Twenty-eighth Day of June, 2022

Katherine Kelly Vidal
*Director of the United States Patent and Trademark Office*